(12) United States Patent
Lee (10) Patent No.: US 10,376,238 B2
(45) Date of Patent: Aug. 13, 2019

(54) SYSTEM AND METHOD FOR CUSTOMIZING A PROBE GRIP FOR AN ULTRASOUND PROBE

(71) Applicant: General Electric Company, Schenectady, NY (US)

(72) Inventor: Warren Lee, Niskayuna, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 735 days.

(21) Appl. No.: 14/961,903

(22) Filed: Dec. 8, 2015

(65) Prior Publication Data

US 2017/0156694 A1 Jun. 8, 2017

(51) Int. Cl.
| | |
|---|---|
| *A61B 8/00* | (2006.01) |
| *B29C 67/00* | (2017.01) |
| *B33Y 50/02* | (2015.01) |
| *B33Y 80/00* | (2015.01) |
| *B33Y 10/00* | (2015.01) |
| *B33Y 30/00* | (2015.01) |
| *B33Y 40/00* | (2015.01) |
| *B33Y 50/00* | (2015.01) |
| *B29L 31/46* | (2006.01) |

(52) U.S. Cl.
CPC ............ *A61B 8/4455* (2013.01); *B33Y 10/00* (2014.12); *B33Y 30/00* (2014.12); *B33Y 40/00* (2014.12); *B33Y 50/00* (2014.12); *B33Y 50/02* (2014.12); *B33Y 80/00* (2014.12); *B29L 2031/463* (2013.01)

(58) Field of Classification Search
CPC .... B33Y 50/00; B33Y 80/00; B29L 2031/463
See application file for complete search history.

(56) References Cited

U.S. PATENT DOCUMENTS

| | | | |
|---|---|---|---|
| 4,128,951 | A | 12/1978 | Tansill |
| 4,520,581 | A | 6/1985 | Irwin et al. |
| 5,897,503 | A | 4/1999 | Lyon et al. |
| 7,744,497 | B2 | 6/2010 | Phelan, Jr. |
| 8,838,268 | B2 | 9/2014 | Friedman et al. |
| 2011/0119868 | A1 | 5/2011 | Lalonde |
| 2014/0236335 | A1 | 8/2014 | Lewis et al. |
| 2015/0165690 | A1 | 6/2015 | Tow |
| 2015/0169120 | A1 | 6/2015 | Sanchez et al. |
| 2016/0179062 | A1* | 6/2016 | Marchione ............. G05G 9/047 700/85 |

(Continued)

FOREIGN PATENT DOCUMENTS

WO 2003037448 A1 5/2003

OTHER PUBLICATIONS

Kawanaka H et al.,"A proposal of 3D analytical method for designing a comfortable grip form", Virtual Systems and Multimedia (VSMM), 2010 16th International Conference on, pp. 267-273, Oct. 20-23, 2010, Seoul.

(Continued)

*Primary Examiner* — Mark A Connolly (57) ABSTRACT

A method for customizing a probe grip of an ultrasound probe for a user is presented. The method includes printing the probe grip in a three-dimensional shape of the probe grip based on grip data corresponding to the user. Further, the method includes installing the printed probe grip on the ultrasound probe.

19 Claims, 5 Drawing Sheets

(56) References Cited

U.S. PATENT DOCUMENTS

2017/0030677 A1* 2/2017 Faifer .................. F41A 9/59

OTHER PUBLICATIONS

Chuankai Liu et al.,"Vision-Based 3-D Grasping of 3-D Objects With a Simple 2-D Gripper", Systems, Man, and Cybernetics: Systems, IEEE Transactions on, vol. 44, Issue: 5, pp. 605-620, May 2014.

SDMS, "SDMS Speaks Out for Sonographers at OSHA Hearings on Ergonomics Injury Rules", https://www.sdms.org/msi/osha.asp, Retrieved on Sep. 23, 2015, 6 Pages.

* cited by examiner

SYSTEM AND METHOD FOR CUSTOMIZING A PROBE GRIP FOR AN ULTRASOUND PROBE

BACKGROUND

Embodiments of the present specification relate generally to an ultrasound probe, and more particularly to a system and method for customizing a probe grip for the ultrasound probe.

Medical diagnostic ultrasound is an imaging modality that employs ultrasound waves to probe acoustic properties of biological tissues by producing corresponding images. Particularly, ultrasound systems are used to provide an accurate visualization of muscles, tendons, and other internal organs to assess their size, structure, movement, and/or any pathological conditions using near real-time images. Moreover, owing to the ability to image the underlying tissues without the use of ionizing radiation, ultrasound systems find extensive use in angiography and prenatal scanning.

Typically, ultrasound systems employ an ultrasound probe for transmitting and receiving ultrasound signals from a target volume in a subject or a patient. Further, these ultrasound signals are processed by a processing unit in the ultrasound systems to obtain a quality image of the subject. Moreover, for ultrasound exams, a user, such as a sonographer, may have to hold and manipulate the ultrasound probe at one or more locations and/or positions over the subject/patient for a period of time. Also, the user may be required to perform repeated ultrasound exams throughout the day. However, due to poor ergonomic working conditions, the user may experience repetitive strain injuries. A major portion of these poor ergonomic working conditions for the user may be attributed to handling of the ultrasound probe.

In conventional ultrasound systems, a probe grip may influence the ergonomics of the ultrasound probe. Also, despite differences in the size and shape of users' hands, the probe grip is designed with a single shape and size. Consequently, different users having different sizes of hands are expected to use ultrasound probes with similar probe grips, thereby causing discomfort and pain for the user. Also, over a period of time, working with incorrect probe grip, the user may experience multiple strain injuries.

BRIEF DESCRIPTION

In accordance with aspects of the present specification, a method for customizing a probe grip of an ultrasound probe for a user is presented. The method includes printing the probe grip in a three-dimensional shape of the probe grip based on grip data corresponding to the user. Further, the method includes installing the printed probe grip on the ultrasound probe.

In accordance with a further aspect of the present specification, a system for customizing a probe grip of an ultrasound probe for a user is presented. The system includes a processor configured to process grip data corresponding to the user associated with a three-dimensional shape of the probe grip. Further, the system includes a three dimensional printer coupled to the processor and configured to print the probe grip in the three-dimensional shape based on the processed grip data.

In accordance with another aspect of the present specification, an ultrasound probe is presented. The ultrasound probe includes at least a transducer array of transducer elements configured to transmit and receive ultrasound signals from a target volume. Also, the ultrasound probe includes a probe grip installed over a portion of the ultrasound probe, wherein the probe grip is customized based on one or more parameters of a user.

In accordance with yet another aspect of the present specification, an imaging system is presented. The imaging system includes an acquisition subsystem configured to obtain image data corresponding to a target volume in an object of interest and including at least an ultrasound probe. Further, the ultrasound probe includes at least an array of transducer elements configured to transmit and receive ultrasound signals from a target volume, and a probe grip installed over a portion of the ultrasound probe, wherein the probe grip is customized based on one or more parameters of a user. In addition, the imaging system includes a processing subsystem in operative association with the acquisition subsystem and configured to process the acquired image data to generate one or more images corresponding to the target volume in the object of interest.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

As will be described in detail hereinafter, various embodiments of exemplary systems and methods for customizing a probe grip for an ultrasound probe are presented. In particular, the probe grip is customized as per the shape and size of a user's hand. By customizing the probe grip, ergonomics of the ultrasound probe may be significantly improved, which in turn minimizes strain injuries to the user. Also, the user may examine a subject/patient without experiencing any pain or discomfort associated with the probe grip.

Figure 1:
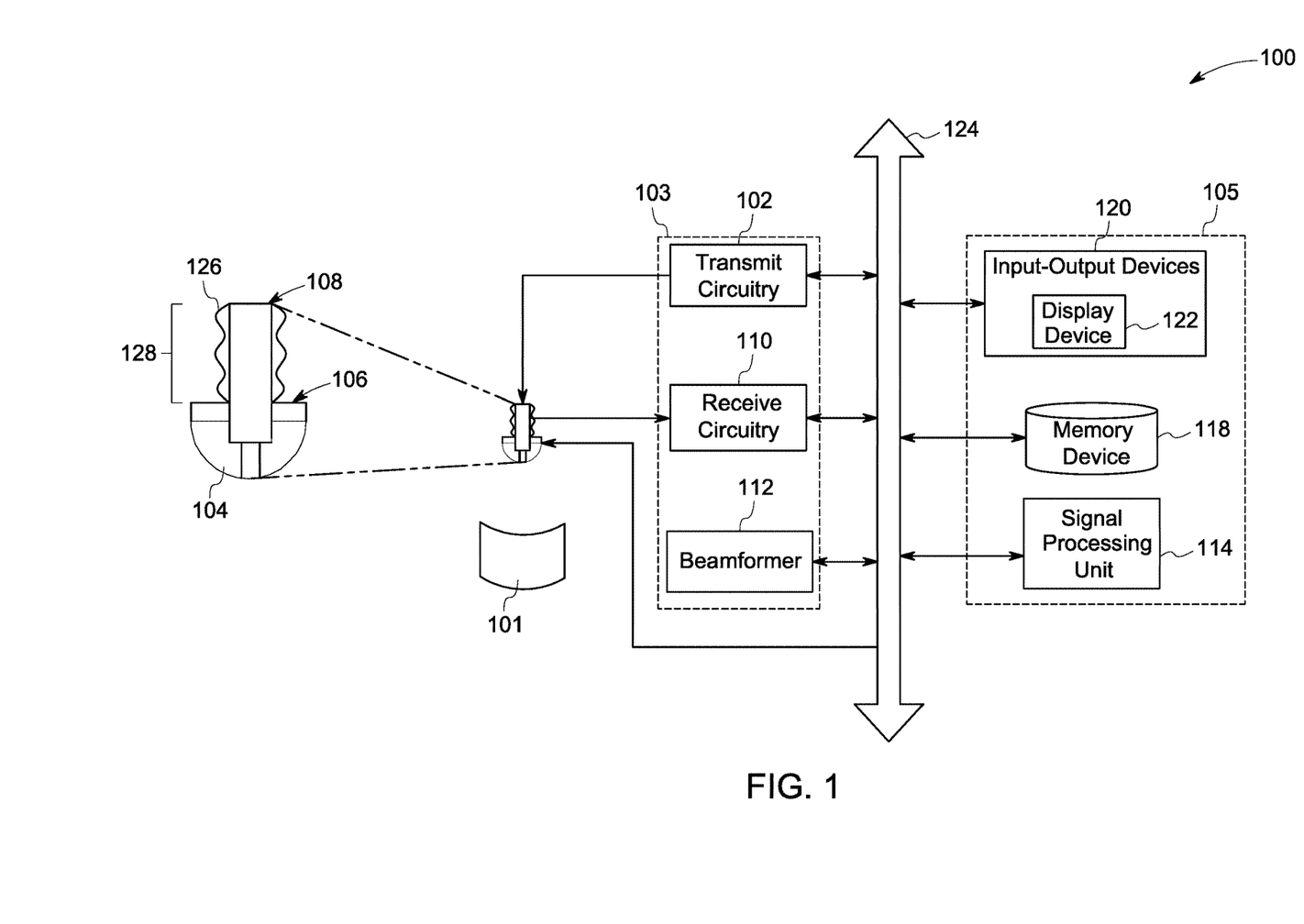
FIG. 1 is a diagrammatical representation of an ultrasound system for imaging a target volume in a subject, in accordance with aspects of the present specification.

FIG. 1 illustrates an ultrasound system 100 for imaging a target volume 101 in a subject. In one embodiment, the ultrasound system 100 may be configured as a console system or a cart-based system. Alternatively, the ultrasound system 100 may be configured as a portable system, such as a hand-held, laptop-style and/or a smartphone-based system. For ease of description, the ultrasound system 100 is represented as a portable ultrasound system.

Further, in the present specification, the ultrasound system 100 is presented as being used to image a target volume 101 in biological tissues of interest. In one example, the target volume 101 may include cardiac tissues, liver tissues, breast tissues, prostate tissues, thyroid tissues, lymph nodes, vascular structures adipose tissue, muscular tissue, and/or blood cells. Alternatively, the system 100 may be employed for imaging non-biological materials such as manufactured parts, plastics, aerospace composites, and/or foreign objects within a body such as a catheter or a needle.

In certain embodiments, the system 100 includes an acquisition subsystem 103 and a processing subsystem 105. The acquisition subsystem 103 is configured to obtain image data corresponding to a target volume 101 in an object of interest. Further, the processing subsystem 105 is configured to process the acquired image data to generate one or more images corresponding to the target volume 101 in the object of interest. The acquisition subsystem 103 includes transmit circuitry 102, receive circuitry 110, and a beamformer 112. The processing subsystem 105 includes a signal processing unit 114, a memory device 118, and input-output devices 120.

In a presently contemplated configuration, the transmit circuitry 102 generates a pulsed waveform to drive a transducer array 104 of transducer elements 106 housed within an ultrasound probe 108. Particularly, the pulsed waveform drives the transducer array 104 of transducer elements 106 to emit ultrasonic pulses into the target volume 101. The transducer elements 106, for example, may include piezoelectric, piezoceramic, capacitive, and/or microfabricated crystals. At least a portion of the ultrasonic pulses generated by the transducer elements 106 is back-scattered from the target volume 101 to produce echoes that return to the transducer array 104 and are received by receive circuitry 110 for further processing. It may be noted that the terms "ultrasonic" and "ultrasound" may be used interchangeably in the following description.

Also, in the embodiment illustrated in FIG. 1, the receive circuitry 110 is coupled to a beamformer 112 that processes the received echoes and outputs corresponding radio frequency (RF) signals. Subsequently, a signal processing unit 114 receives and processes the RF signals in near real-time and/or offline mode. The signal processing unit 114 includes devices such as one or more general-purpose or application-specific processors, digital signal processors, microcomputers, microcontrollers, Application Specific Integrated Circuits (ASICs), Field Programmable Gate Arrays (FPGA), or other suitable devices in communication with other components of the system 100.

Moreover, in certain embodiments, the signal processing unit 114 also provides control and timing signals for configuring one or more imaging parameters for imaging the target volume 101 in the subject. Furthermore, in one embodiment, the signal processing unit 114 stores the delivery sequence, frequency, time delay, and/or beam intensity, for example, in a memory device 118 for use in imaging the target volume 101. The memory device 118 includes storage devices such as a random access memory, a read only memory, a disc drive, solid-state memory device, and/or a flash memory. In one embodiment, the signal processing unit 114 uses the stored information for configuring the transducer elements 106 to direct one or more groups of pulse sequences toward the target volume 101. Subsequently, the signal processing unit 114 tracks the displacements in the target volume 101 caused in response to the incident pulses to determine corresponding tissue characteristics. The displacements and tissues characteristics, thus determined, are stored in the memory device 118. The displacements and tissues characteristics may also be communicated to a medical practitioner, such as a radiologist, for further diagnosis.

In some embodiments, the signal processing unit 114 may be further coupled to one or more user input-output devices 120 for receiving commands and inputs from an operator, such as the medical practitioner. The input-output devices 120, for example, may include devices such as a keyboard, a touchscreen, a microphone, a mouse, a control panel, a display device 122, a foot switch, a hand switch, and/or a button. In one embodiment, the signal processing unit 114 processes the RF signal data to prepare image frames and to generate the requested medically relevant information based on user input. Particularly, the signal processing unit 114 may be configured to process the RF signal data to generate two-dimensional (2D) and/or three-dimensional (3D) datasets corresponding to different imaging modes.

Further, the signal processing unit 114 may be configured to reconstruct desired images from the 2D or 3D datasets. Subsequently, the signal processing unit 114 may be configured to display the desired images on the associated display device 122 that may be communicatively coupled to the signal processing unit 114. The display device 122, for example, may be a local device. Alternatively, in one embodiment, the display device 122 may be remotely located to allow a remotely located medical practitioner to access the reconstructed images and/or medically relevant information corresponding to the target volume 101 in the subject/patient. It may be noted that the various components of the ultrasound system 100 are communicatively coupled via a communication channel 124.

Moreover, during ultrasound examinations, a user, such as a sonographer, may have to hold and manipulate the ultrasound probe at one or more locations and/or positions over the subject/patient. Also, the user may be required to perform repeated ultrasound exams throughout the day. Due to poor ergonomic working conditions, the user may experience repetitive strain injuries. Particularly, due to different size and shape of users' hand, a probe grip of the ultrasound probe may adversely affect the ergonomics of the ultrasound probe. This in turn may cause discomfort to the user during scanning of the subject/patient. Also, the use of such probe grips may result in multiple strain injuries to the user over a period of time.

To overcome the above problems or shortcomings, the exemplary ultrasound system 100 includes a probe grip 126 that is customized as per the size and shape of an individual user's hand. The probe grip 126 may be an external grip that is installed over a portion 128 of the ultrasound probe 108, where the user holds the ultrasound probe 108 during the ultrasound exams more specifically, grip data associated with one or more parameters of the user is received or computed. In one example, the parameters of the user may include a size of the user's hand and/or fingers, a grip style of the user, and gaps/space between the fingers when the user holds the probe 108. Further, the probe grip 126 is designed and printed based on the grip data. In one example, a three-dimensional (3D) printer is used to print or mold the probe grip 126. Furthermore, the printed probe grip 126 is installed over the ultrasound probe 108, which is later used by the user for holding the probe 108. As the probe grip 126 is customized as per the user's requirement, the user may perform ultrasound exams without any discomfort and/or pain. The aspect of customizing the probe grip 126 will be described in greater detail with reference to FIGS. 2-4.

Figure 2:
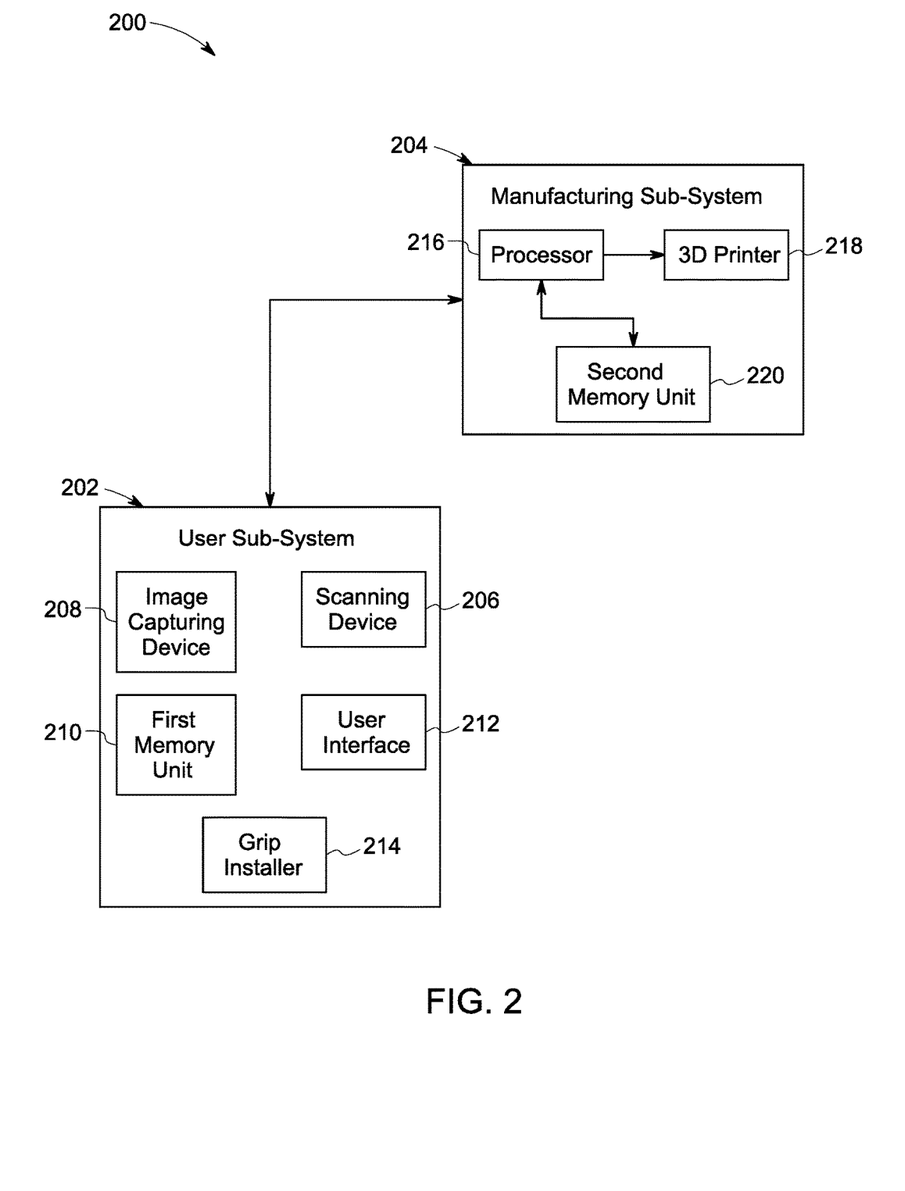
FIG. 2 is a diagrammatical representation of a system for customizing a probe grip, in accordance with aspects of the present specification.

Referring to FIG. 2, a diagrammatical representation of a system 200 for customizing a probe grip, in accordance with aspects of the present specification, is depicted. For ease of understanding, the system 200 is described with reference to the components of FIG. 1. The system 200 includes a user sub-system 202 and a manufacturing sub-system 204. The user sub-system 202 may be configured to provide a grip data to the manufacturing subsystem 204. In one example, the user sub-system 202 may be a combination of components that is used by the user for communicating the grip data to the manufacturing subsystem 204. On the other hand, the manufacturing sub-system 204 may be configured to customize the probe grip 126 based on the received grip data. In one example, the grip data may be a data corresponding to a size of the user's hand and a grip style of the user.

In a presently contemplated configuration, the user sub-system 202 may include components, such as a scanning device 206, an image capturing device 208, a first memory unit 210, and a user interface 212. It may be noted that the user sub-system 202 may use one or more of these components to provide the grip data to the manufacturing sub-system 204. In one embodiment, the scanning device 206 may be used to scan impressions of the user's fingers on a mock-up unit. In one example, the mock-up unit may be a dummy probe grip having a deformable outer surface. Further, the scanning device 206 may send this scanned data as the grip data to the manufacturing sub-system 204. The aspect of providing the grip data using the scanning device 206 will be explained in greater detail with reference to FIG. 3.

In another embodiment, the image capturing device 208 may be used to capture a three-dimensional (3D) image of the user gripping the mock-up unit. This 3D image may include an image of the user's fingers, gaps/space between the fingers, and a portion of the mock-up unit. Further, the image capturing device 208 may communicate this 3D image as the grip data to the manufacturing sub-system 204. The aspect of providing the grip data using the image capturing device 208 will be explained in greater detail with reference to FIG. 4.

In yet another embodiment, the first memory unit 210 may store a plurality of hand sizes and a plurality of grip styles. In one example, a grip style may be indicative of a style of the user holding the ultrasound probe 108. Further, the user may use the user interface 212 to select one of the hand sizes and one of the grip styles. In one example, the user may send an input signal to select a hand size and a grip style that are corresponding to the user via the user interface 212 or a remote device. Further, the first memory unit 210 may communicate the selected hand size and the grip style as the grip data to the manufacturing sub-system 204. In one example, the first memory unit 210 in conjunction with a transmitter or a transceiver may communicate the grip data to the manufacturing sub-system 204. The aspect of providing the grip data using the first memory unit 210 will be explained in greater detail with reference to FIG. 5.

At the other end, the manufacturing sub-system 204 is configured to customize the probe grip based on the grip data. In one exemplary embodiment, the manufacturing sub-system 204 includes a processor 216, a three-dimensional (3D) printer 218, and a second memory unit 220. The processor 216 may be configured to receive the grip data from the user sub-system 202. This grip data may be received from the scanning device 206, the image capturing device 208, and/or the first memory unit 210 of the user sub-system 202. Further, the processor 216 may process this grip data to determine a three-dimensional (3D) shape of the probe grip. In one example, the processor 216 may use one or more algorithms or software stored in the second memory unit 220 to determine the 3D shape of the probe grip. Furthermore, the processor 216 may send printing data associated with the 3D shape of the probe grip to the 3D printer 218.

The 3D printer 218 may print the probe grip in the 3D shape based on the received printing data. In one example, the 3D printer 218 may mold a gripping material into the three-dimensional shape of the probe grip. Also, in one example, gripping material may be fabricated from materials such as polymers, thermoplastics, rubbers, silicones, and/or thermoplastic elastomers.

Upon printing or molding the probe grip, the manufacturing sub-system 204 may send this printed or molded probe grip to the user sub-system 202 for installing on the ultrasound probe 108. At the user sub-system 202, a grip installer 214 may be used to install the probe grip over a grip portion 128 of the ultrasound probe 108. In one example, the manufacturing sub-system 204 may install this probe grip on the ultrasound probe 108. Further, the manufacturing sub-system 204 may send this ultrasound probe 108 to the user. In one embodiment, the manufacturing sub-system 104 may use the 3D printer 218 to print the probe grip as a plurality of sub-sections. Further, these sub-sections are fastened or coupled to an outer surface of the ultrasound probe 108 to form the probe grip.

Thus, by employing the exemplary system 200, the probe grip may be customized as per the user's hand and grip style. By customizing the probe grip, ergonomics of the ultrasound probe 108 may be significantly improved, which in turn minimizes strain injuries in the user. Also, the user may examine a subject/patient without any pain or discomfort.

Figure 3:
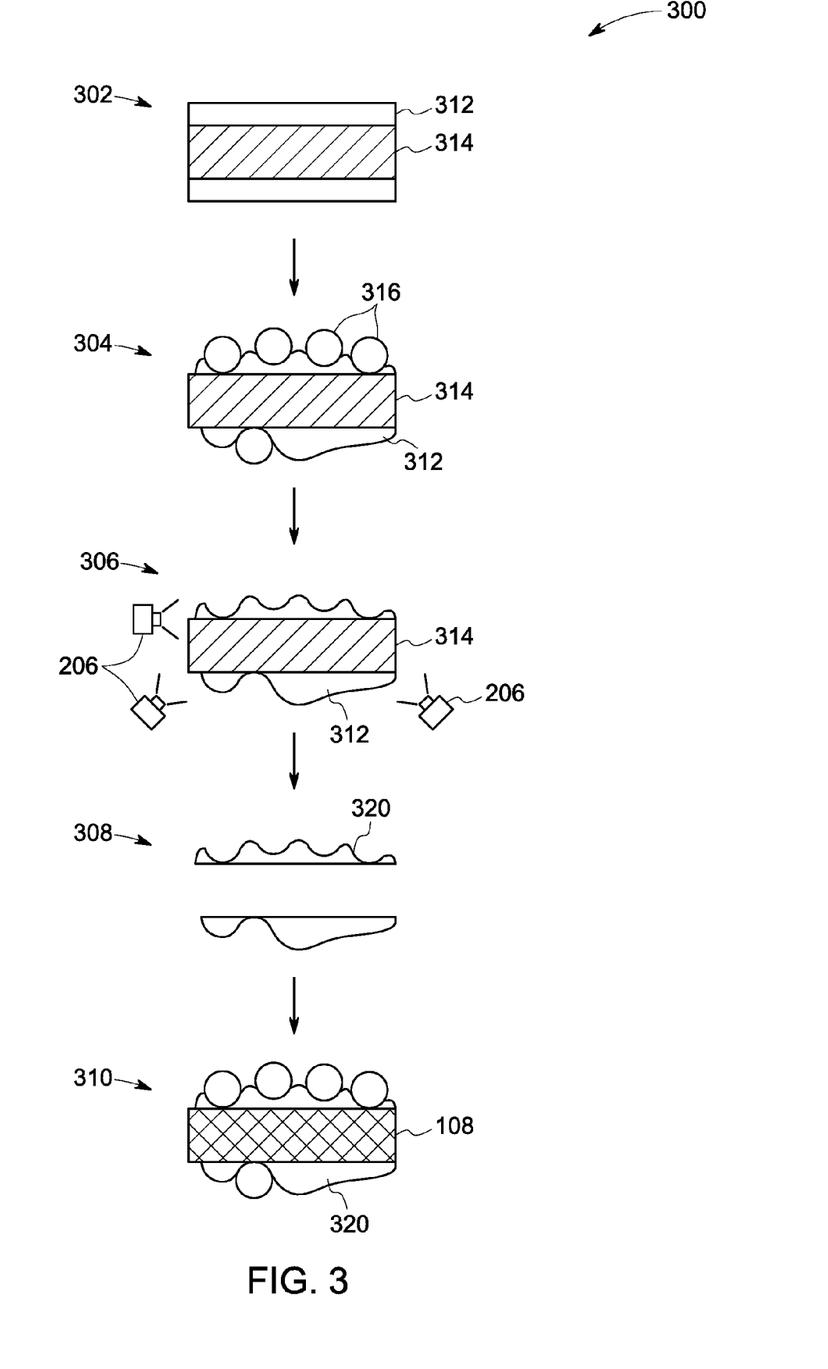
FIG. 3 is a schematic representation of an exemplary method for customizing the probe grip, in accordance with aspects of the present specification.

FIG. 3 illustrates different stages of a method for customizing a probe grip, in accordance with one embodiment of the present specification. For ease of understanding, the method 300 is described with reference to the components of FIGS. 1 and 2.

The method begins at a first stage 302, where a deformable segment 312 is disposed around a mock-up unit 314. In one embodiment, the deformable segment 312 may be presented as an outer layer of the mock-up unit 314. In one example, the deformable segment 312 may be referred to as a moldable segment that is capable of changing its shape as per an applied grip of a user. In one embodiment, a manufacturer may ship the mock-up unit 314 having the deformable segment 312 to the user. It may be noted that the mock-up unit 314 may be a cylindrical housing that is capable of housing a grip portion 128 of the ultrasound probe 108.

Subsequently, at a second stage 304, grip data associated with the three-dimensional shape of the probe grip is translated onto the deformable segment. By way of example, the user may grip or hold the mock-up unit 314 in a desired manner to translate the grip data onto the deformable segment. Particularly, the user may place their fingers 316 on the deformable segment 312 to hold or grip the mock-up unit 314. When the user holds the mock-up unit 314, a determined pressure is applied on the deformable segment 312 that is disposed on an outer surface of the mock-up unit 314. This determined pressure may in turn deform or mold the deformable segment 312 into a three-dimensional (3D) shape, where the 3D shape is a signature of the user's grip. In one example, the deformable segment 312 may have an impression of the fingers 316 of the user holding the mock-up unit 314. Thus, the 3D shape of the deformable segment 312 corresponds to a size of the user's fingers as well as the grip style of the user holding the mock-up unit 314.

Furthermore, at a third stage 306, the mock-up unit 314 along with the deformable segment 312 having the user's grip signature may be scanned by a scanning device 206 at the user sub-system 202. Particularly, the deformable segment 312 that is molded or deformed on the outer surface of the mock-up unit 314 may be 3D scanned by the scanning device 206 to capture the details of the 3D shape of the deformable segment 312.

Additionally, at a fourth stage 308, the scanning device 206 may communicate this 3D scanned data associated with the 3D shape of the deformable segment 312 to the manufacturing sub-system 204. In one example, the scanning device 206 may transmit this 3D scanned data as the grip data to the processor 216 in the manufacturing sub-system 204. Further, the processor 216 in the manufacturing sub-system 204 may process this scanned 3D data to determine a three-dimensional (3D) shape of a probe grip 320. In one example, the processor 216 may use one or more algorithms or software stored in a second memory unit 220 to determine the 3D shape of the probe grip 320. Furthermore, the processor 216 may send printing data associated with the 3D shape of the probe grip 320 to the 3D printer 218. In one embodiment, the 3D scanned data may be directly communicated to the 3D printer 218 without using the processor 216. Upon receiving the printing data or 3D scanned data, the 3D printer 218 may print the probe grip 320 in the 3D shape that is desired by the user. In one example, the 3D printer 218 may mold a gripping material into the 3D shape of the probe grip 320.

Subsequently, at a fifth stage 310, the printed probe grip 320 may be made available for installing on the ultrasound probe 108. In certain embodiments, the manufacturer may install this printed probe grip 320 on the ultrasound probe 108. Further, the manufacturer may send the ultrasound probe 108 having this printed probe grip 320 to the user. Alternatively, the probe grip 320 may be provided to the user for installing on the ultrasound probe 108. In one example, the grip installer 214 may be used to install this probe grip 320 on the ultrasound probe 108. In some embodiments, the probe grip 320 may be printed as one or more sub-sections of the probe grip 320. Further, these sub-sections of the probe grip 320 may be fastened to on an outer surface of the probe 108 as the probe grip 320.

Thus, by employing the exemplary method, the probe grip 320 may be customized as desired by the user. Also, by using the customized probe grip 320, the user may not experience pain or discomfort otherwise experienced with conventional probe grips while scanning the patient/subject. Moreover, if a new user wishes to use the ultrasound probe 108, the probe grip 320 may be easily replaced with a new probe grip that is customized as per the requirement of the new user. Thus, the ultrasound probe 108 may be rendered ergonomically suitable for more than one user by providing customized probe grips for the same ultrasound probe.

Figure 4:
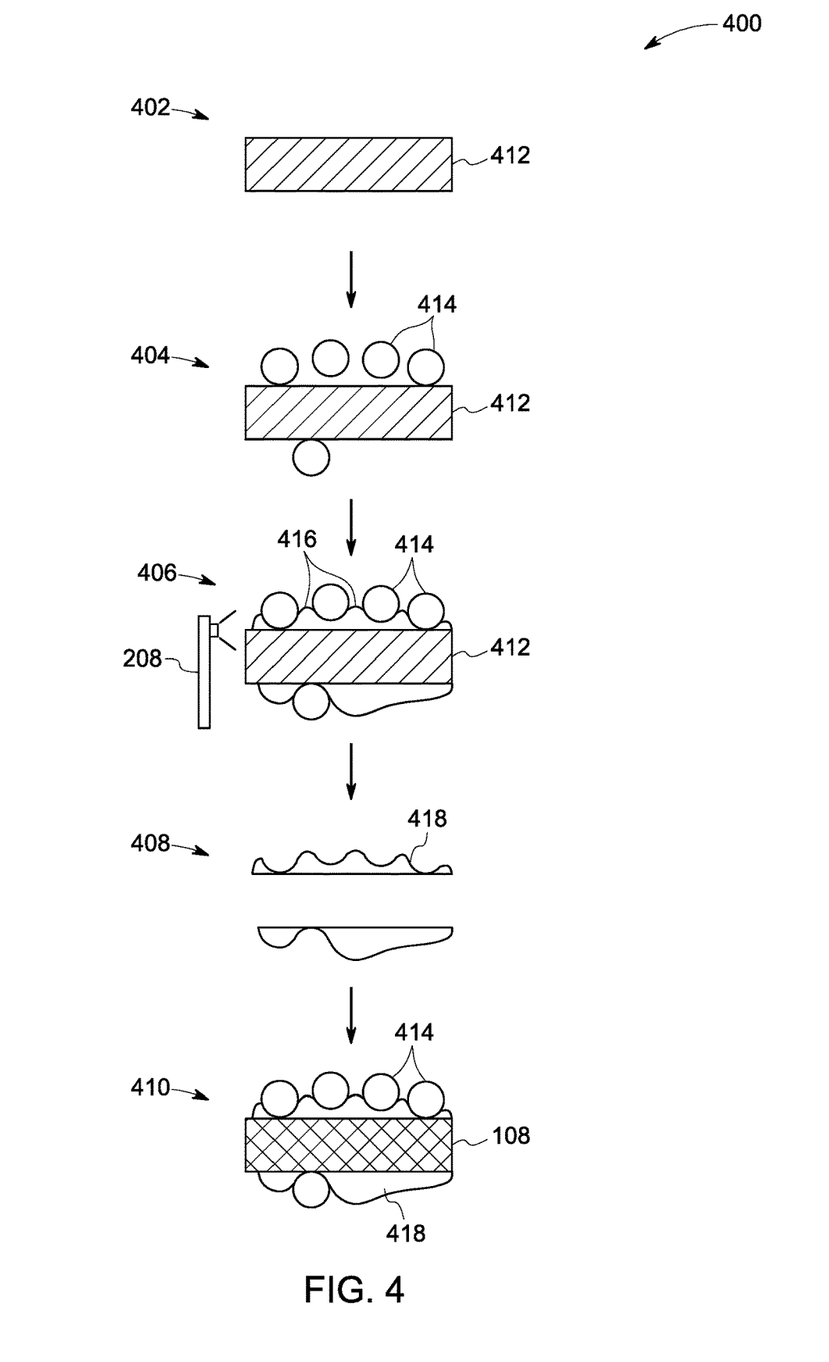
FIG. 4 is a schematic representation of another exemplary method for customizing the probe grip, in accordance with aspects of the present specification.

FIG. 4 illustrates different stages of a method 400 for customizing the probe grip, in accordance with another embodiment of the present specification. For ease of understanding, the method 400 is described with reference to the components of FIGS. 1 and 2.

The method 400 begins at a first stage 402, where a mock-up unit 412 is sent to a user of the ultrasound probe 108. In one example, the mock-up unit 412 may be a cylindrical housing that is capable of housing a grip portion 128 of the ultrasound probe 108. The mock-up unit 412 may be sent to the user by a manufacturer. Optionally, the manufacturer may send a glove along with the mock-up unit 412 to the user. The glove may be a tight fitting glove that is designed with a predetermined color and/or pattern. In one example, a color of the glove is different from a color of the outer surface of the mock-up unit 412. This difference in the colors of the glove and the outer surface of the mock-up unit 412 aids in differentiating between the user's hand/fingers and the outer surface of the mock-up unit 412. Also, this difference in the colors of the glove and the outer surface of the mock-up unit 412 enables easy identification/determination of gaps/spaces between the fingers when the user holds the mock-up unit 412.

Subsequently, at a second stage 404, the user may grip or hold the mock-up unit 412 in a manner similar to that of holding an ultrasound probe for examining a patient, for example optionally, the user may wear a glove and then grip or hold the mock-up unit 412 in the desired manner. Reference numeral 414 is generally representative of the fingers of the user.

Additionally, at a third stage 406, an image capturing device such as the image capturing device 208 in the user sub-system 202 may be used to capture an image of the user gripping or holding the mock-up unit 412. In one example, a smart phone having a camera and/or a sensor may be used as the image capturing device 208. Particularly, the smart phone may be used to detect and record the position of user's hand/fingers on the mock-up unit 412. In one embodiment, the image capturing device 208 may capture an image of the user holding the mock-up unit 412 with the glove. In this embodiment, the captured image may visually depict gaps 416 between the fingers 414 on the mock-up unit 412 and gaps between the fingers 414 and the mock-up unit 412.

Furthermore, at a fourth stage 408, the image capturing device 208 may communicate this captured image to the manufacturing sub-system 204. In one example, the image capturing device 208 may transmit this captured image as grip data to the processor 216 in the manufacturing sub-system 204. Also, the processor 216 in the manufacturing sub-system 204 may process this captured image to determine a three-dimensional (3D) shape of a probe grip 418. In one example, the processor 216 may use one or more algorithms or software stored in the second memory unit 220 to determine the 3D shape of the probe grip 418. Furthermore, the processor 216 may send printing data associated with the 3D shape of the probe grip 418 to the 3D printer 218. In one embodiment, the captured image data may be directly communicated to the 3D printer 218 without using the processor 216. Upon receiving the printing data or the captured image, the 3D printer 218 may print the probe grip 418 in the 3D shape that is desired by the user. In one example, the 3D printer 218 may mold a gripping material into the three-dimensional shape of the probe grip 418.

Subsequently, at a fifth stage 410, the printed probe grip 418 may be sent to the user for installing on the ultrasound probe 108. In one embodiment, the user may use the grip installer 214 in the user sub-system 202 to install or slide the probe grip 418 over the ultrasound probe 108. In another embodiment, the manufacturer may install this printed probe grip 418 on the ultrasound probe 108. In one example, the manufacturer may attach the printed probe grip 418 to one or more sides of the ultrasound probe. Further, the manufacturer may send the ultrasound probe 108 having this printed probe grip 418 to the user. In another embodiment, the manufacturer may print the probe grip 418 as one or more sub-sections. Further, these sub-sections are fastened to the outer surface of the probe as the probe grip 418.

Figure 5:
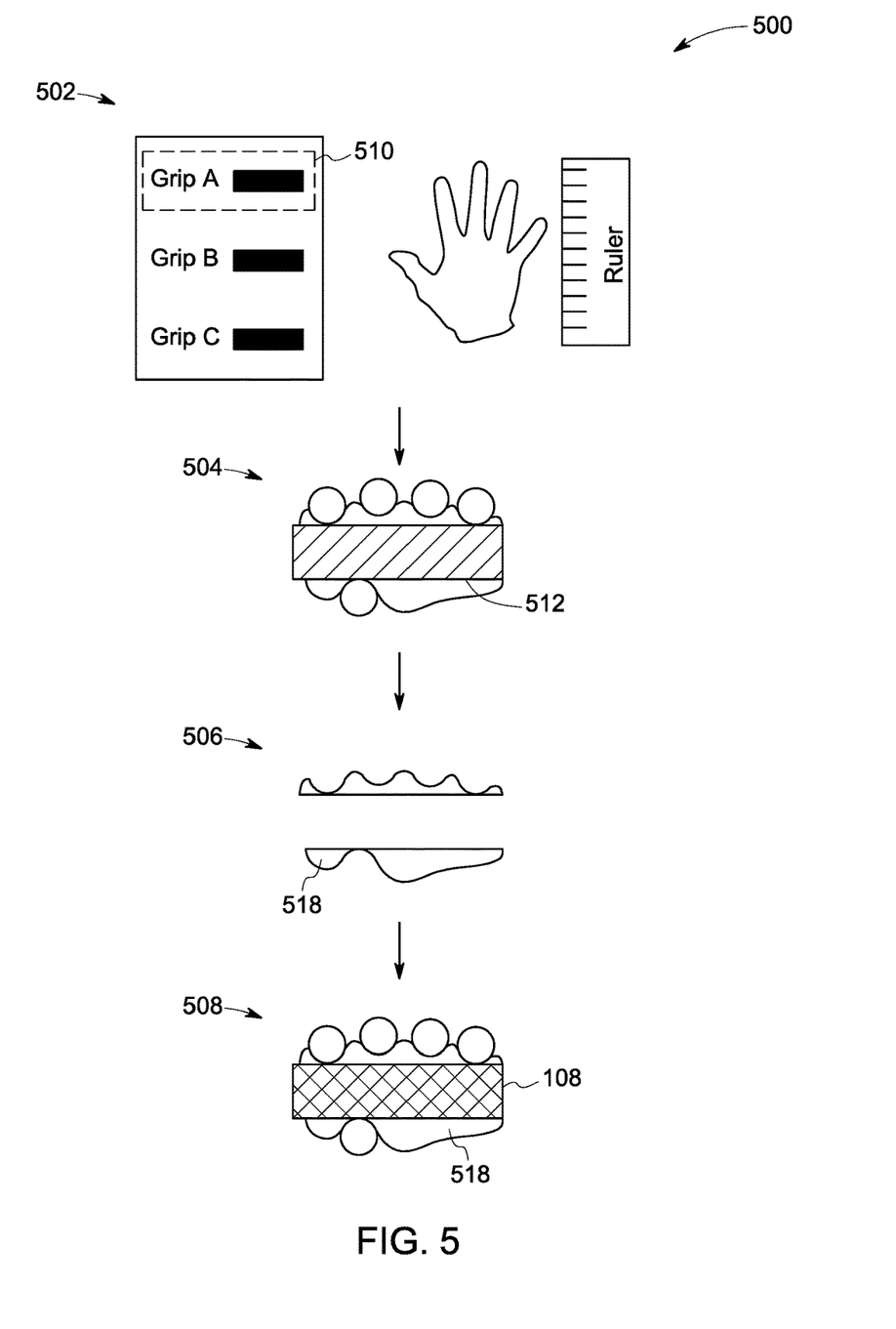
FIG. 5 is a schematic representation of yet another exemplary method for customizing the probe grip, in accordance with aspects of the present specification.

FIG. 5 illustrates different stages of a method 500 for customizing a probe grip, in accordance with one embodiment of the present specification. For ease of understanding, the method 500 is described with reference to the components of FIGS. 1 and 2.

The method beings at a first stage 502, where a user may select a hand size from a plurality of hand sizes. Also, the user may select a grip style from a plurality of grip styles. Particularly, the first memory unit 210 in the user sub-system 202 may be configured to store the plurality of hand sizes and the plurality of grip styles. Further, the user may use the user interface 212 of the user sub-system 202 to select one of the hand sizes and/or one of grip styles. FIG. 5 depicts the user selecting "Grip A" as the user's grip style 510. In one example, the user may send an input signal from a remote device or the user interface 212 to select a hand size and a grip style that correspond to the user. Further, the first memory unit 210 may communicate the selected hand size and the grip style as the grip data to the manufacturing sub-system 204. In one example, the first memory unit 210 in conjunction with a transmitter may communicate the grip data to the manufacturing sub-system 204.

Subsequently, at a second stage 504, the processor 216 in the manufacturing sub-system 204 may determine a 3D grip model 512 based on the selected hand size and the grip style of the user. In one embodiment, the processor 216 may use one or more algorithms or software stored in the second memory unit 220 to determine the 3D grip model 512. In another embodiment, the processor 216 may determine the 3D grip model 512 based on a combination of the selected hand size, the grip style, and a predetermined dimension of the ultrasound probe.

Additionally, at a third stage 506, the processor 216 may send data associated with the determined 3D grip model 512 to the 3D printer 218 to print a probe grip 518 in the 3D shape that is desired by the user. In one example, the 3D printer 218 may mold a material for the grip into the 3D shape of the probe grip 518.

Subsequently, at a fourth stage 508, the printed probe grip 518 may be sent to the user for installation on the ultrasound probe 108. In one embodiment, the manufacturer may install this printed probe grip 518 on the ultrasound probe 108. In one example, the manufacturer may attach the printed probe grip 518 to one or more sides of the ultrasound probe. Further, the manufacturer may send the ultrasound probe 108 having this printed probe grip 518 to the user. In another embodiment, the manufacturer may print the probe grip 518 as one or more sub-sections. Further, these sub-sections are assembled or fastened to the outer surface of the probe 108 as the probe grip 518.

The various embodiments of the exemplary systems and methods aid in customizing the probe grip as required by the user. By customizing the probe grip, ergonomics of the ultrasound probe may be significantly improved, which in turn minimizes strain injuries in the user. Also, the user may examine a subject/patient without feeling the discomfort that is otherwise felt due to off-the-shelf probe grips that are not customized, and hence may not be ergonomically suitable for the user. Additionally, different users can use the same probe by merely changing the probe grip that is customized for each individual user.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for customizing a probe grip of an ultrasound probe for a user, the method comprising:
   receiving a grip data associated with a three-dimensional shape of the probe grip, wherein receiving the grip data comprises capturing a three-dimensional image of the user gripping a mock-up unit;
   printing the probe grip in the three-dimensional shape of the probe grip based on grip data corresponding to the user; and
   installing the printed probe grip on the ultrasound probe.

2. The method of claim 1, further comprising determining gaps between fingers of the user gripping the mock-up unit and gaps between the fingers and the mock-up unit based on the captured three-dimensional image.

3. The method of claim 1, wherein printing the probe grip in the three-dimensional shape comprises communicating the received grip data to a three-dimensional printer to print the three-dimensional shape of the probe grip.

4. The method of claim 1, wherein installing the printed probe grip on the ultrasound probe comprises sliding or attaching the printed probe grip to the ultrasound probe.

5. The method of claim 1, wherein installing the printed probe grip on the ultrasound probe comprises:
   manufacturing a plurality of sub-sections associated with the probe grip; and
   fastening the plurality of sub-sections to an outer surface of the ultrasound probe.

6. A method for customizing a probe grip of an ultrasound probe for a user, the method comprising:
   receiving a grip data associated with a three-dimensional shape of the probe grip, wherein the receiving the grip data comprises:
      receiving at least a hand size and a grip style associated with the user of the ultrasound probe;
      determining a grip model based on the hand size and the grip style;
   printing the probe grip in the three-dimensional shape of the probe grip based on the grip data corresponding to the user; and
   installing the printed probe grip on the ultrasound probe.

7. The method of claim 6, wherein receiving at least the hand size and the grip style comprises:
   selecting the d size from a plurality of hand sizes; and
   selecting the grip style from a plurality of grip styles.

8. The method of claim 6, wherein printing the probe grip in the three-dimensional shape comprises communicating the received grip data to a three-dimensional printer to print the three-dimensional shape of the probe grip.

9. The method of claim 6, wherein installing the printed probe grip on the ultrasound probe comprises sliding or attaching the printed probe grip to the ultrasound probe.

10. The method of claim 6, wherein installing the printed probe grip on the ultrasound probe comprises:
    manufacturing a plurality of sub-sections associated with the probe grip; and
    fastening the plurality of sub-sections to an outer surface of the ultrasound probe.

11. A system for customizing a probe grip of an ultrasound probe for a user, the system comprising:
    an image capturing device configured to capture a three-dimensional image of the user gripping a mock-up unit as a grip data corresponding to the user;
    a processor configured to process the grip data corresponding to the user associated with a three-dimensional shape of the probe grip; and
    a three-dimensional printer coupled to the processor and configured to print the probe grip in the three-dimensional shape based on the processed grip data.

12. The system of claim 11, wherein the processor is configured to process the three-dimensional image to determine gaps between fingers of the user gripping the mock-up unit.

13. The system of claim 11, where the image capturing device is configured to communicate the grip data to the processor.

14. The system of claim 11, further comprising a grip installer configured to install the printed probe grip on the ultrasound probe.

15. A system for customizing a probe grip of an ultrasound probe for a user, the system comprising:
- a memory unit configured to store a plurality of hand sizes and a plurality of grip styles;
- a user interface coupled to the memory unit and configured to select a hand size from the plurality of hand sizes and a grip style from the plurality of grip styles based on an input signal provided by the user as a grip data corresponding to the user;
- a processor configured to process the grip data corresponding to the user associated with a three-dimensional shape of the probe grip; and
- a three-dimensional printer coupled to the processor and configured to print the probe grip in the three-dimensional shape based on the processed grip data.

16. The system of claim 15, where in the memory unit is configured to communicate the grip data to the processor.

17. The system of claim 15, further comprising a grip installer configured to install the printed probe grip on the ultrasound probe.

18. An ultrasound probe for a user, comprising:
- at least a transducer array of transducer elements configured to transmit and receive ultrasound signals from a target volume; and
- a customized probe grip installed over a portion of the ultrasound probe, wherein the customized probe grip is customized based on a grip data corresponding to the user, and wherein the grip data comprises at least one of a three-dimensional image of the user gripping a mock-up unit or a hand size associated with the user selected from a plurality of hand sizes and a grip style associated with the user selected from a plurality of grip styles.

19. An imaging system, comprising:
- an acquisition subsystem configured to obtain image data corresponding to a target volume in an object of interest and comprising at least an ultrasound probe for a user, wherein the ultrasound probe comprises:
  - at least an array of transducer elements configured to transmit and receive ultrasound signals from a target volume;
  - a customized probe grip installed over a portion of the ultrasound probe, wherein the customized probe grip is customized based on a grip data corresponding to the user, and wherein the grip data comprises at least one of a three-dimensional image of the user gripping a mock-up unit or a hand size associated with the user selected from a plurality of hand sizes and a grip style associated with the user selected from a plurality of grip styles; and
- a processing subsystem in operative association with the acquisition subsystem and configured to process acquired image data to generate one or more images corresponding to the target volume in the object of interest.

* * * * *